(12) United States Patent
Kang et al.

(10) Patent No.: US 9,619,626 B2
(45) Date of Patent: Apr. 11, 2017

(54) METHOD AND APPARATUS FOR IDENTIFYING EXERCISE INFORMATION OF USER

(71) Applicant: Samsung Electronics Co., Ltd., Gyeonggi-do (KR)

(72) Inventors: Jeong-Gwan Kang, Gyeonggi-do (KR); Sun-Young Park, Gyeonggi-do (KR); Nam-Hoon Kim, Gyeonggi-do (KR); Hyeon-Seong Kim, Seoul (KR); Hyun-Su Hong, Gyeonggi-do (KR); Myung-Sik Kim, Gyeonggi-do (KR)

(73) Assignee: Samsung Electronics Co., Ltd (KR)

(*) Notice: Subject to any disclaimer, the term of this patent is extended or adjusted under 35 U.S.C. 154(b) by 563 days.

(21) Appl. No.: 14/150,326

(22) Filed: Jan. 8, 2014

(65) Prior Publication Data
US 2014/0195018 A1 Jul. 10, 2014

Related U.S. Application Data

(60) Provisional application No. 61/750,082, filed on Jan. 8, 2013.

(30) Foreign Application Priority Data

Nov. 18, 2013 (KR) .................. 10-2013-0139952

(51) Int. Cl.
| | |
|---|---|
| *A63F 13/00* | (2014.01) |
| *G06F 19/00* | (2011.01) |
| *A61B 5/11* | (2006.01) |

(52) U.S. Cl.
CPC ........ *G06F 19/3481* (2013.01); *A61B 5/1123* (2013.01); *A61B 2560/0242* (2013.01); *A61B 2562/0219* (2013.01)

(58) Field of Classification Search
USPC ....................................... 463/31–42
See application file for complete search history.

(56) References Cited

U.S. PATENT DOCUMENTS

| | | | |
|---|---|---|---|
| 7,383,082 B2 | 6/2008 | Kawanishi et al. | |
| 7,548,161 B2 | 6/2009 | Wehrenberg | |
| 8,180,591 B2 | 5/2012 | Yuen et al. | |
| 8,180,592 B2 | 5/2012 | Yuen et al. | |

(Continued)

FOREIGN PATENT DOCUMENTS

| | | |
|---|---|---|
| JP | 11347021 | 12/1999 |
| JP | 2004267535 | 9/2004 |

(Continued)

*Primary Examiner* — Masud Ahmed
(74) *Attorney, Agent, or Firm* — The Farrell Law Firm, P.C.

(57) ABSTRACT

A method and a user terminal for identifying exercise information of a user are provided. The method includes detecting air pressure information at a location of the user terminal; identifying a state of a topography at the location of the user terminal by using the detected air pressure information; analyzing vertical movement and horizontal movement of the user terminal to identify movement information of the user terminal; and identifying the exercise information of the user according to the identified movement information of the user terminal and the identified state of the topography at the location of the user terminal.

20 Claims, 5 Drawing Sheets

(56) References Cited

U.S. PATENT DOCUMENTS

| | | | |
|---|---|---|---|
| 8,311,770 B2 | 11/2012 | Yuen et al. | |
| 2006/0064277 A1 | 3/2006 | Jung et al. | |
| 2006/0256076 A1 | 11/2006 | Liou et al. | |
| 2009/0005220 A1 | 1/2009 | Lee et al. | |
| 2011/0152363 A1 | 6/2011 | Jang | |
| 2012/0004883 A1 | 1/2012 | Vock et al. | |
| 2012/0083715 A1 | 4/2012 | Yuen et al. | |
| 2012/0083716 A1 | 4/2012 | Yuen et al. | |
| 2012/0190386 A1* | 7/2012 | Anderson | G01C 15/04 455/456.3 |
| 2013/0343585 A1* | 12/2013 | Bennett | H04R 25/554 381/315 |
| 2014/0052567 A1* | 2/2014 | Bhardwaj | G06Q 30/0631 705/26.7 |
| 2015/0258370 A1* | 9/2015 | Arkush | A61B 5/087 482/8 |
| 2016/0153853 A1* | 6/2016 | Brenner | G01L 5/047 702/155 |

FOREIGN PATENT DOCUMENTS

| | | |
|---|---|---|
| KR | 100653315 | 11/2006 |
| KR | 1020100068779 | 6/2010 |
| KR | 1020110070751 | 6/2011 |
| KR | 1020120082301 | 7/2012 |

\* cited by examiner

METHOD AND APPARATUS FOR IDENTIFYING EXERCISE INFORMATION OF USER

PRIORITY

This application claims priority under 35 U.S.C. §119(e) to U.S. Provisional Patent Application Ser. No. 61/750,082, which was filed in the United States Patent and Trademark Office on Jan. 8, 2013, and claims priority under 35 U.S.C. §119(a) to Korean Application Serial No. 10-2013-0139952, which was filed in the Korean Intellectual Property Office on Nov. 18, 2013, the entire contents of each of which are incorporated herein by reference.

BACKGROUND

1. Field of the Invention

The present invention relates to a technology for identifying information of a user in a user terminal, and more particularly, to a method and an apparatus for identifying exercise information of a user by using a sensor included in a user terminal.

2. Description of the Related Art

Recently, there has been a gradual expansion of various services and functions provided by user terminals, such as mobile devices. In order to increase an effective value of user terminals and to meet various demands of users, various applications executable in user terminals have been developed.

A user terminal is able to store and execute basic applications produced by a manufacturer of the corresponding device and installed in the corresponding device, as well as additional applications downloaded from web sites that sell the applications through the Internet. The additional applications may be developed by general developers and registered in the websites that sell applications. Accordingly, anyone can freely sell applications developed by himself/herself to the user of the user terminal, through the websites that sell applications. Therefore, tens of thousands to hundreds of thousands of applications are currently provided to the user terminals free of charge or at a cost.

Since the user terminal tends to be personalized, the user carries the user terminal for a considerably long time in his/her daily life. In consideration of such a fact, applications that analyze a movement pattern of the user terminal to predict an amount of exercise of the user are developed.

However, the application that predicts the amount of exercise of the user generally uses data detected by a motion sensor to predict the exercise amounts of the user, and thus the exercise amounts are roughly predicted. As a result, the application has a limitation in accurately predicting the exercise amounts of the user. Further, in order to predict the amount of exercise of the user, a processor should be continuously driven to analyze the movement pattern of the user terminal even though the user does not control the user terminal while moving, whereby a lot of power is consumed.

SUMMARY OF THE INVENTION

The present invention has been made to address the above problems and/or disadvantages and to provide at least the advantages described below. Accordingly, an aspect of the present invention provides an apparatus and a method for stably identifying exercise information of the user by using a sensor hub having relatively small power consumption.

According to an aspect of the present invention, a method of identifying exercise information of a user of a user terminal is provided. The method includes detecting air pressure information at a location of the user terminal; identifying a state of a topography at the location of the user terminal by using the detected air pressure information; analyzing vertical movement and horizontal movement of the user terminal to identify movement information of the user terminal; and identifying the exercise information of the user according to the identified movement information of the user terminal and the identified state of the topography at the location of the user terminal.

According to another aspect of the present invention, a user terminal identifying exercise information of a user is provided. The user terminal includes an air pressure sensor configured to detect air pressure information at a location of the user terminal; a motion sensor configured to detect vertical movement and horizontal movement of the user terminal; and a sensor processor configured to process a program for identifying exercise information of the user by using data detected from the air pressure sensor and the motion sensor, wherein the program for identifying the exercise information of the user comprises a command for identifying a state of a topography at the location of the user terminal by using the detected air pressure information, analyzing the vertical movement and the horizontal movement of the user terminal to identify movement information of the user terminal, and identifying the exercise information of the user according to the identified movement information of the user terminal and the identified state of the topography at the location of the user terminal.

BRIEF DESCRIPTION OF THE DRAWINGS

The above and other aspects, features, and advantages of the present invention will be more apparent from the following detailed description taken in conjunction with the accompanying drawings, in which.

DETAILED DESCRIPTION

Figure 1:
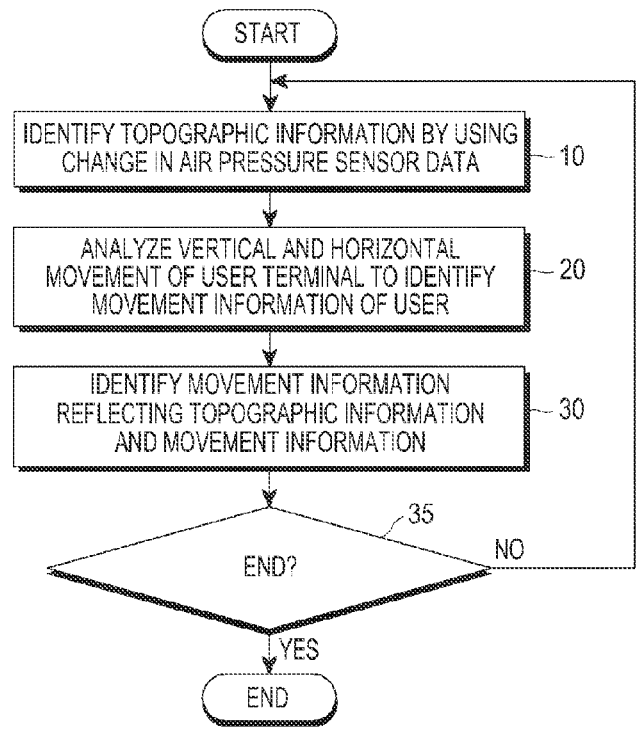
FIG. 1 is a flowchart illustrating a sequence of a user exercise information identifying method according to an embodiment of the present invention.

Hereinafter, embodiments of the present invention will be described with reference to the accompanying drawings. However, the present invention is not restricted or limited by these embodiments. The same or similar components may be designated by the same or similar reference numerals although they are illustrated in different drawings. Detailed descriptions of constructions or processes known in the art may be omitted to avoid obscuring the subject matter of the present invention. While terms including ordinal numbers, such as "first" and "second," etc., may be used to describe various components, such components are not limited by the above terms. The terms are used merely for the purpose to distinguish an element from the other elements. For example, a first element could be termed a second element, and similarly, a second element could be also termed a first element without departing from the scope of the present invention. The terms used in this application is for the purpose of describing particular embodiments only and is not intended to be limiting of the invention. As used herein, the singular forms are intended to include the plural forms as well, unless the context clearly indicates otherwise.

Figure 2:
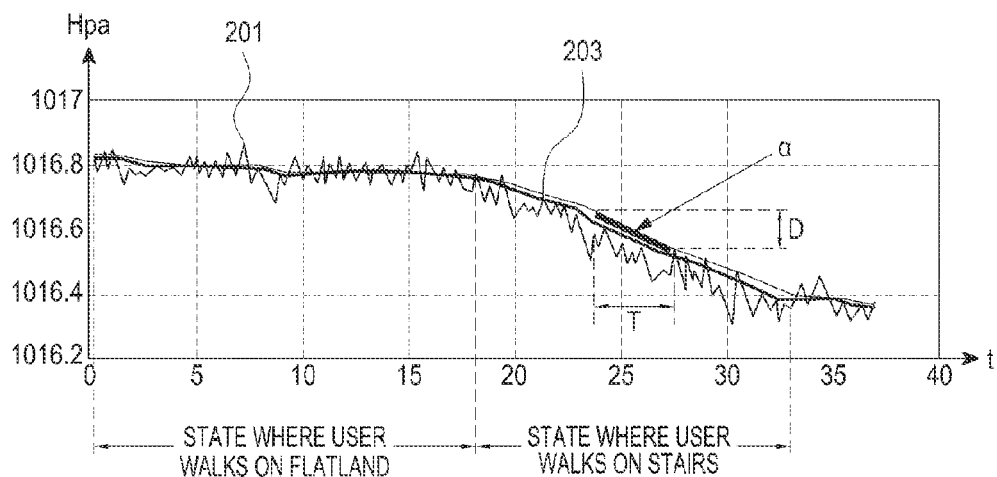
FIG. 2 is a graph illustrating air pressure sensor data measured by a user exercise information identifying method according to an embodiment of the present invention.

FIG. 1 is a flowchart illustrating a sequence of a user exercise information identifying method according to an embodiment of the present invention. FIG. 2 is a graph illustrating air pressure sensor data measured by a user exercise information identifying method according to an embodiment of the present invention Referring to FIG. 1, the user exercise information identifying method according to the embodiment of the present invention includes identifying, at step 10, information on a topography where a user has moved (hereinafter referred to as "topographic information") and identifying, at step 20, movement information of the user.

In step 10, the topographic information may be identified using air pressure information of the user terminal, which is carried by the user. The air pressure information corresponds to information on pressure applied to the user terminal, and may be data (hereinafter referred to as "air pressure sensor data") measured and provided by an air pressure sensor included in the user terminal. For example, the air pressure sensor data is measured with respect to units of a predetermined time, so that a wide variation of air pressure sensor data is generated according to a movement state (walking, running, or the like) of the user. Accordingly, as shown in FIG. 2, in step 10, the air pressure sensor data (i.e., original data 201) is applied to a low pass filter having a predetermined size and low pass-filtered data 203 is collected for a predetermined time T. Further, a difference value D of air pressure sensor data between a start point and an end point of the predetermined time and information α regarding a change in the air pressure sensor data during the collection are identified from the low pass-filtered data 203. In addition, the topographic information is identified using the difference value D of the air pressure sensor data and the information α regarding the change in the air pressure sensor data.

The topographic information may include a topographic state indicating whether the topography of an area to which the user has moved is a flatland or a slope. The topographic state may be identified by using the difference value D of the air pressure sensor data and the information α on the change in the air pressure sensor data. More specifically, the topographic state may be identified by using a degree of sloping determined using the difference value D of the air pressure sensor data and the information α on the change in the air pressure sensor data. When the degree of sloping identified using the difference value D of the air pressure sensor data and the information α on the change in the air pressure sensor data is at least equal to a predetermined threshold, the topographic state is determined as a "slope". When the degree of sloping is less than the predetermined threshold, the topographic state may be determined as a "flatland".

The user may carry the user terminal in various ways, such as when the user puts the user terminal into a bag, puts the user terminal into a pocket, or grasps the user terminal by hand while moving. When the user carries the user terminal in various ways while moving, the air pressure sensor data may be generated as different values that vary according to manner in which the terminal is carried. Further, the air pressure sensor data of the user terminal carried by the user may have different values according to an individual physical feature of the user or exercise intensity. As variance of the air pressure sensor data diversely changes due to such various factors, there may be errors in the determined topographic state. According to an embodiment of the present invention, in order to reduce the error in the determined topographic state, the topographic state may be determined after a reference corresponding to a predefined condition is variably changed.

Figure 3A:
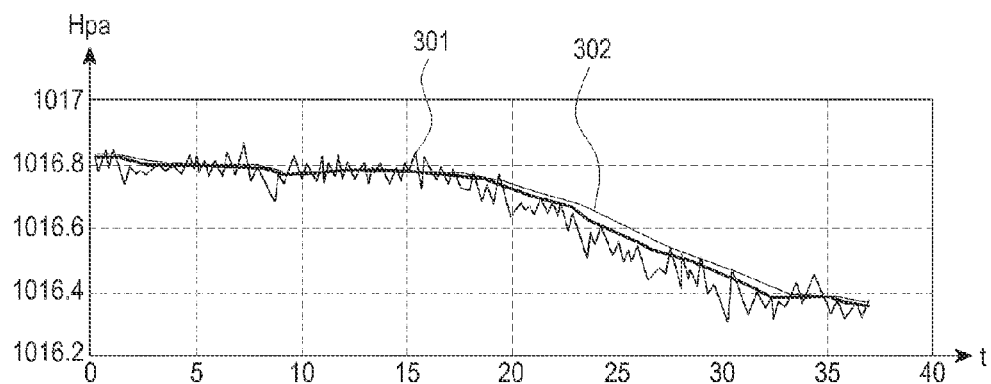
FIG. 3A is a graph illustrating air pressure sensor data measured in a state where a user walks on a slope by a user exercise information identifying method according to an embodiment of the present invention.
Figure 3B:
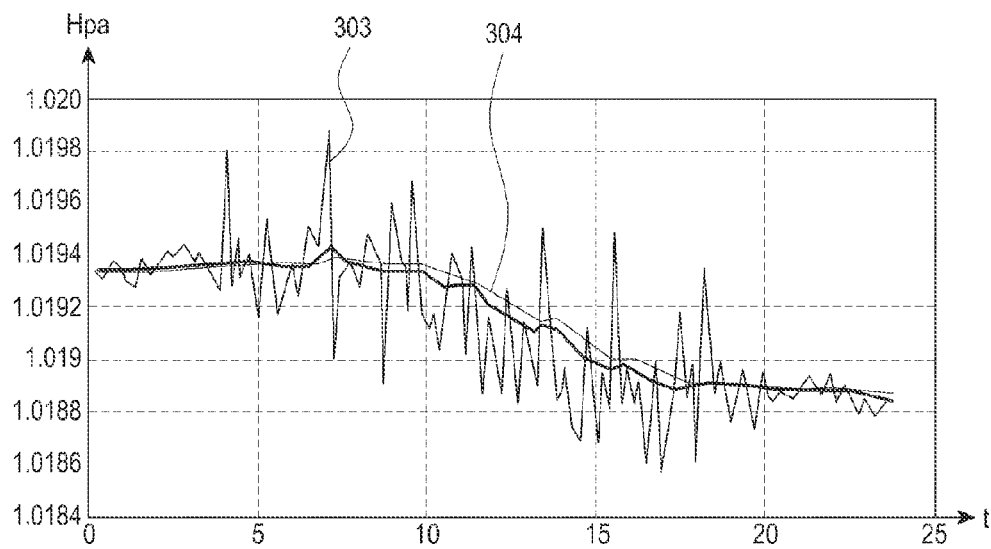
FIG. 3B is a graph illustrating air pressure sensor data measured in a state where a user runs on a slope by a user exercise information identifying method according to an embodiment of the present invention.
Figure 4A:
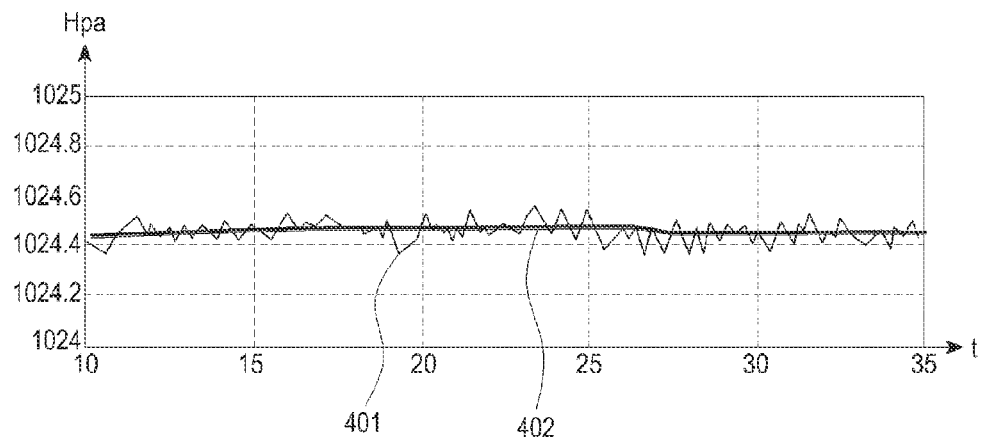
FIG. 4A is a graph illustrating air pressure sensor data measured in a state where a user walks on a flatland by a user exercise information identifying method according to an embodiment of the present invention.

FIG. 3A is a graph illustrating air pressure sensor data measured in a state where the user walks on a slope in a user exercise information identifying method according to an embodiment of the present invention, and FIG. 3B is a graph illustrating air pressure sensor data measured in a state where the user runs on the slope in the user exercise information identifying method according to an embodiment of the present invention. FIG. 4A is a graph illustrating air pressure sensor data measured in a state where the user walks on a flatland in a user exercise information identifying method according to an embodiment of the present invention, and FIG. 4B is a graph illustrating air pressure sensor data measured in a state where the user runs on the flatland in the user exercise information identifying method according to an embodiment of the present invention.

Referring to FIGS. 3A and 3B first, air pressure sensor data (i.e., original data 301) has a relatively larger variance in a state where the user is running on a slope, such as in FIG. 3B, relative to a variance in a state where the user is walking on the slope, such as in FIG. 3A. However, low pass-filtered data 303 generated by applying the air pressure sensor data (i.e., original data 301) to a low pass filter having a predetermined size has little variance, thereby enabling a stable analysis of a topographic state.

Figure 4B:
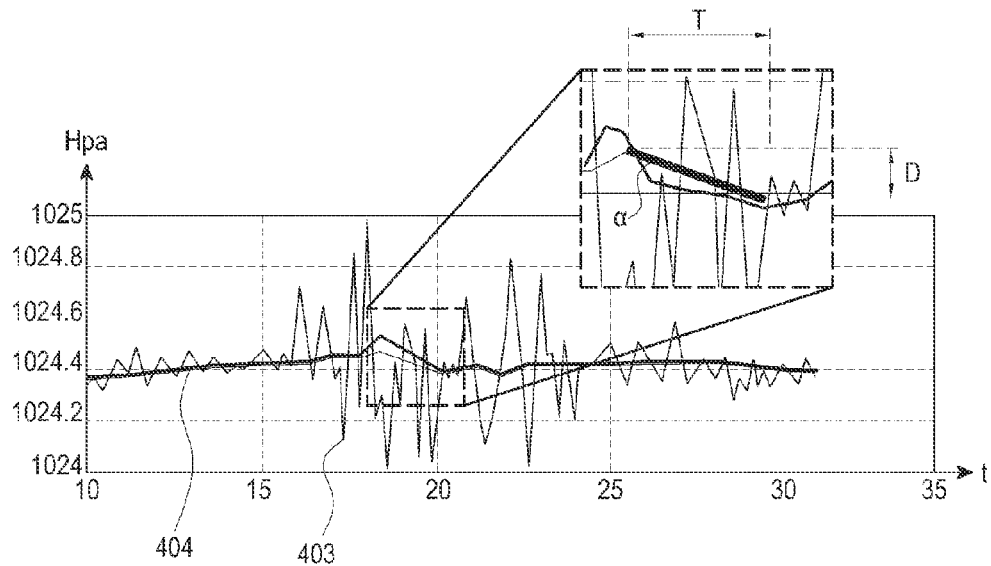
FIG. 4B is a graph illustrating air pressure sensor data measured in a state where a user runs on a flatland by a user exercise information identifying method according to an embodiment of the present invention.

Referring to FIGS. 4A and 4B, air pressure sensor data (i.e., original data 401) has a relatively larger variance in a state where the user is running on a flatland, such as in FIG. 4B, relative to a variance in a state where the user walks on the flatland, such as in FIG. 4A. However, low pass-filtered data 403 generated by applying the air pressure sensor data (i.e., original data 401) to a low pass filter having a predetermined size has little variance, thereby enabling a stable analysis of a topographic state. As described above, according to an embodiment of the present invention, the topographic information regarding a location to which the user has moved can be detected using air pressure information of the user terminal carried by the user.

Meanwhile, in step 20 of FIG. 1, the movement information may be identified by analyzing a vertical or horizontal movement of the user terminal carried and moved by the user. Further, the vertical or horizontal movement of the user terminal may be identified through sensor data input from a sensor included in the user terminal. For example, the movement information may include a movement state, which may include information regarding a "running" state, a "walking" state, etc. For example, when a vertical or horizontal acceleration data value provided from an acceleration sensor included in the user terminal is at least equal to a predetermined threshold, the movement information may be identified as the "running" state, and when the acceleration data value is less than the predetermined threshold, the movement information may be identified as the "walking" state.

Although the above-described embodiment of the present invention refers to a movement state as a "walking" state or a "running" state, embodiments of the present invention are not limited thereto, and various modifications can be made in accordance with embodiments of the present invention. For example, the movement state may be any of a "normal walking" state, a "quick walking" state, or a "running" state, and accordingly, there may be a plurality of predetermined threshold values to distinguish between these states.

Further, although the above-described embodiment of the present invention refers to movement information that is determined using vertical or horizontal acceleration data value provided from an acceleration sensor, embodiments of the present invention are not limited thereto, and various modifications can be made in accordance with embodiments of the present invention. For example, the user may carry the user terminal in various ways, including putting the user terminal into a bag, a pocket, or grasping the user terminal by hand while moving. As described above, by taking into consideration that the user moves while carrying the user terminal in various ways, the movement information can be more accurately identified using data provided from a gyro sensor or a geo-magnetic sensor. For example, by identifying and applying a direction in which the user moves through the use of the data provided from the gyro sensor or the geo-magnetic sensor, the movement information of the user terminal can be more accurately identified, even though the user carries the user terminal in various ways.

The movement information may further include a step count. The step count may be identified through a periodic pattern of the data provided from an acceleration sensor, a gyro sensor, or a geo-magnetic sensor. For example, in response to a movement of the user, data provided from the acceleration sensor, the gyro sensor, or the geo-magnetic sensor may have a predetermined periodic pattern. The predetermined periodic pattern may be a sinusoidal pattern repetitively oscillating between a maximum value, an origin, and a minimum value. Based on the pattern, one cycle of a sine waveform detected from the data provided by the acceleration sensor, the gyro sensor, or the geo-magnetic sensor may be counted as one step.

Further, a movement state of the user may be determined by considering the step count. For example, the movement state of the user may be determined as a "running" state or a "walking" state according to the step count within a predetermined time. For example, when the step count is detected as being up to 2.5 steps per second, the movement state may determined as the "walking" state, and when the step count is detected as being greater than 2.5 steps per second, the movement state may be determined as the "running" state.

Referring back to FIG. 1, after performing step 20, the user exercise information identifying method proceeds to step 30, in which exercise information is identified.

When the user does not actually move on their own, but instead moves due to being in a moving object (e.g., an elevator, an escalator, an automobile, a ship, etc.), the topographic state may be identified as a "slope" or a "flatland" according to a change in a value input from the air pressure sensor. Accordingly, exercise information may be erroneously calculated even though the user is not actually moving on his/her own. Therefore, according to an embodiment of the present invention, the exercise information may be identified in consideration of the topographic information identified through the air pressure sensor and the movement state of the user identified through the motion sensor in step 30 of identifying the exercise information. For example, when the movement state of the user is determined to be one of the "running" state or the "walking" state, the amount of exercise and burnt calories of the user may be identified in consideration of whether the topographic state is identified as one of a "slope" or a "flatland".

Further, the amount of exercise and burnt calories of the user may vary according to whether the user moves on a slope or flatland. When the user moves on a slope, the amount of exercise and burnt calories of the user may vary according to whether the user moves on an ascent of the slope or a descent of the slope. Further, when the user moves on the slope, the amount of exercise and burnt calories of the user may be different according to an angle of the slope. Accordingly, step 30 of identifying the exercise information may be performed in consideration of the topographic information identified in step 10 and the movement information identified in step 20. For example, the exercise information may be identified according to situations shown in Table 1 below, by considering the topographic information identified in step 10 and the movement information identified in step 20. More specifically, as described above, a weight or a constant parameter value used for calculating the amount of exercise and burnt calories of the user may vary according to each of the situations.

TABLE 1

| Topographic information | | Movement state | Situation |
| --- | --- | --- | --- |
| Slope | Ascent | Running | Situation 1-1 |
| | | Walking | Situation 1-2 |
| | Descent | Running | Situation 2-1 |
| | | Walking | Situation 2-2 |
| | Flatland | Running | Situation 3-1 |
| | | Walking | Situation 3-2 |

Meanwhile, the sloping angle may be detected according to a change in the air pressure identified while the user terminal is moving. More specifically, a length (hereinafter referred to as a "vertical movement distance") between a maximum point and a minimum point in an area where the user terminal has moved is identified using the pressure generated while the user terminal is moving. Further, a step count (StepCount) is identified according to the movement, and the step count (StepCount) is multiplied by a predetermined pace (StepLength) so as to identify a length (hereinafter, referred to as a "slope movement distance") of the slope of an area to which the user has moved. Thereafter, the sloping angle (SlopeAngle) may be identified by applying the vertical movement distance (MovingDistanceVertical) and the slope movement distance (MovingDistanceSlope) to a trigonometric function in consideration of a relation between the vertical movement distance and the slope movement distance. For example, the sloping angle (SlopeAngle) may be calculated using Equation (1) below:

$$\text{SLOPE ANGLE} = \cos^{-1} \frac{\text{MOVING DISTANCE VERTICAL}}{\text{MOVING DISTANCE SLOPE}} \quad (1)$$

The vertical movement distance (MovingDistanceVertical) may be calculated by Equation (2) below:

$$\text{MOVING DISTANCE VERTICAL} = \epsilon \cdot (\text{PRESSURE START} - \text{PRESSURE END}) \quad (2)$$

In Equation (2), "PressureStart" denotes a pressure value at a start point of the slope, and "PressureEnd" denotes a pressure value at an end point of the slope.

The slope movement distance (MovingDistanceVertical) may be calculated by Equation (3) below. In Equation (3), the slope movement distance (MovingDistanceSlope) corresponds to a distance that the user has moved, and may be used for identifying the amount of exercise and burnt calories of the user.

$$\text{MOVING DISTANCE SLOPE} = \text{STEP COUNT} \cdot \text{STEP LENGTH} \quad (3)$$

The pace (StepLength) may vary according to the movement state of the user (i.e., the "running" state, the "walking" state, etc.). Accordingly, in order to more accurately identify the slope movement distance, the movement state (i.e., the "running" state, the "walking" state, etc.) is reflected in the pace multiplied by the step count when the slope movement distance is detected. Therefore, the calculation of the sloping angle may further include an operation of calculating the pace (StepLength). The calculation of the pace (StepLength) may be performed according to Equation (4) below.

$$\text{STEP LENGTH} = \kappa \cdot (\alpha + \beta \cdot \text{STEP FREQ} + \chi \cdot \text{STEP FREQ}^2) \quad (4)$$

In Equation (4), $\kappa$, $\alpha$, $\beta$, and $\chi$ denote parameters stored in advance and may be constants acquired by a regression analysis method of data on paces and step speeds of a plurality of users. A step frequency (StepFreq,) denotes a step count per unit time and may be detected at intervals of one second, for example.

Finally, the exercise information may include the sloping angle (SlopeAngle) and the slope movement distance (MovingDistanceSlope) as calculated above.

Further, in step 30, calories (hereinafter referred to as "calorie consumption") burnt by the user may be calculated by additionally using the sloping angle (SlopeAngle) and the slope movement distance (MovingDistanceSlope), and the exercise information may further include the calculated calorie consumption. The calorie consumption calculated in step 30 is acquired in consideration of the sloping angle (SlopeAngle) and may be used for more accurately predicting the amount of exercise of the user.

Steps 10 to 30 of FIG. 1 may be initiated or the user terminal initiates the operations of FIG. 1 (e.g., when an application makes a request for initiating a detection of the exercise information) and may end when the user terminal ends the operations of FIG. 1 (e.g., when the application makes a request for ending the detection of the exercise information). In addition, when the application makes a request for providing the exercise information, exercise information detected from a time point when the detection of the exercise information is initiated to a time point when the request for providing the exercise information is performed may be provided. Alternatively, exercise information corresponding to a section (e.g., a time, a place, etc.) required by the application may be provided.

In another example according to an embodiment of the present invention, the user exercise information identifying method may further include, before performance of step 10, a step (not shown) of setting a predetermined section (for example, three minutes) for which the exercise information is detected, in response to the request for initiating the detection of the exercise information by an application requiring the exercise information. Further, steps 10 to 30 may further include a step of repeatedly performing steps 10 to 30 so that the exercise information identified at an interval of the predetermined section (e.g., three minutes) is provided to the application. According to another example, the exercise information may be provided at an interval of the predetermined section (e.g., three minutes) from the time point when an application makes a request for initiating the detection of the exercise information to a time point when the application makes a request for ending the detection of the exercise information.

In another example according to an embodiment of the present invention, the user exercise information identifying method may further include detecting exercise information by considering an "ON" or "OFF" state of the display of the user terminal to which the method is applied. For example, when the display of the user terminal is in the "ON" state, steps 10 to 30 may be continuously performed and the exercise information may be provided to an application making the request for the detection of the exercise information, whenever the step count is counted. When the display of the user terminal is in the "OFF" state, the exercise information is stored for a predetermined time (e.g., twenty minutes) and the exercise information may be provided to the application at an interval of the predetermined time (e.g., twenty minutes).

Although according to various embodiments of the present invention described herein, the exercise information is provided to the application making the request for the detection of the exercise information, embodiments of the present invention are not limited thereto and the topographic information and the movement information may be also provided together with the exercise information in accordance with embodiments of the present invention.

The operations of steps 10 and 20 described herein according to the embodiment of the present invention are satisfied if the movement information and the topographic information can be detected, regardless of the order in which these steps are performed. Accordingly, steps 10 and 20 may be sequentially performed regardless of the order thereof (e.g., step 20 may be performed before or after step 10) or steps 10 and 20 may be simultaneously performed in parallel.

Although, according to various embodiments of the present invention described herein, the topographic state is determined as the "slope" state or the "flatland" state, the present invention is not limited thereto. The topographic state may be variously changed. For example, the topographic state may be determined by stages based on a threshold of a predetermined sloping angle. For example, the topographic state may be determined as a predetermined stage topographic state, such as 1-1 stage topography when the sloping angle is greater than 0 degrees and less than or equal to 10 degrees, 1-2 stage topography when the sloping angle is greater than 0 degrees and less than or equal to −10 degrees, 2-1 stage topography when the sloping angle is greater than 10 degrees and less than or equal to 20 degrees, 2-2 stage topography when the sloping angle is greater than −10 degrees and less than or equal to −20 degrees, 3-1 stage topography when the sloping angle is greater than 20 degrees and less than or equal to 30 degrees, 3-2 stage topography when the sloping angle is greater than −20 degrees and less than or equal to −30 degrees, 4-1 stage topography when the sloping angle is greater than 30 degrees and less than or equal to 40 degrees, 4-2 stage topography when the sloping angle is greater than −30 degrees and less than or equal to −40 degrees, 5-1 stage topography when the sloping angle is greater than 40 degrees and less than or equal to 50 degrees, and 5-2 stage topography when the sloping angle is greater than −40 degrees and less than or equal to −50 degrees.

Although, according to various embodiments of the present invention described herein, the movement state of the user is determined as the "running" state or the "walking" state, embodiments of the present invention are not limited thereto. The determination of the movement state of the user may be changed in various ways. For example, the movement state of the user may be determined by stages based on a predetermined threshold. For example, the movement state may be determined as a predetermined stage movement state, such as a first stage movement when the number of steps per unit time (e.g., one second) is greater than 0 and less than or equal to 1, a second stage movement when the number of steps per unit time is greater than 1 and less than or equal to 2, a third stage movement when the number of steps per unit time is greater than 2 and less than or equal to 3, a fourth stage movement when the number of steps per unit time is greater than 3 and less than or equal to 4, and a fifth stage movement when the number of steps per unit time (for example, one second) is greater than 4 and less than or equal to 5.

Figure 5:
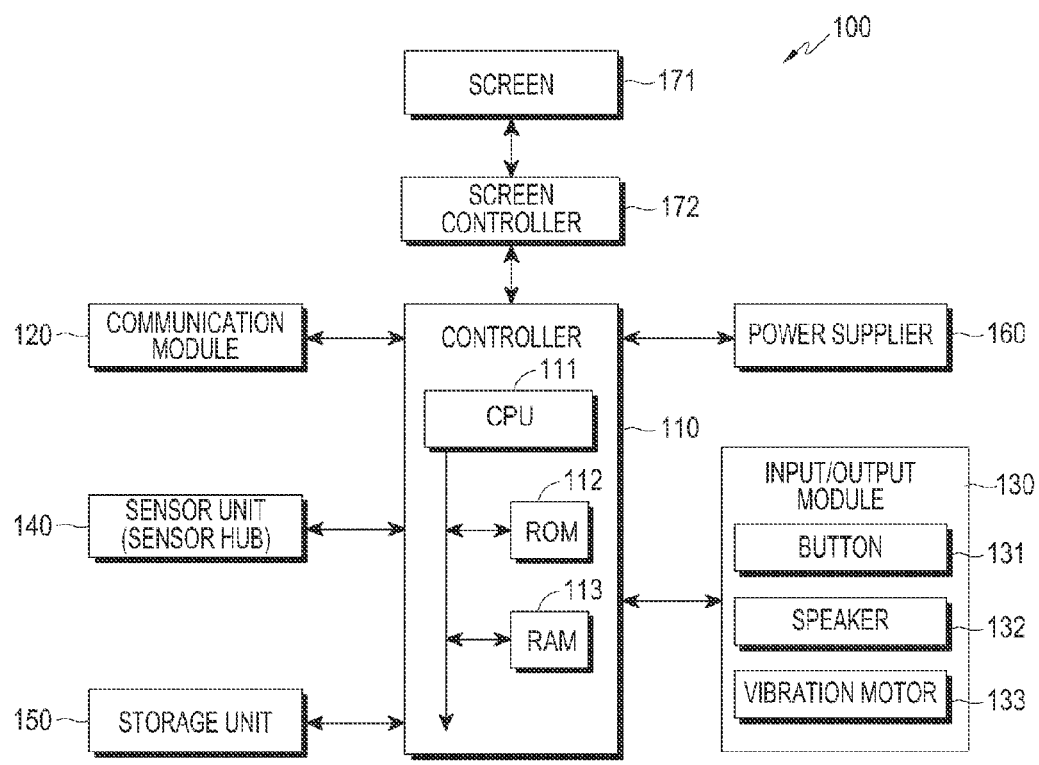
FIG. 5 is a block diagram illustrating a structure of a user terminal to which a user exercise information identifying method is applied according to an embodiment of the present invention.

FIG. 5 is a block diagram illustrating a structure of a user terminal to which a user exercise information identifying method is applied according to an embodiment of the present invention.

Referring to FIG. 5, a user terminal 100 includes a controller 110, a communication module 120, an input/output module 130, a sensor unit (sensor hub) 140, a storage unit 150, a power supplier 160, a screen 171, and a screen controller 172.

The controller 110 includes a Central Processing Unit (CPU) 111, a Read Only Memory (ROM) 112 that stores control programs for controlling the user terminal 100, and a Random Access Memory (RAM) 113 that is used to store signals or data input from outside of the user terminal 100 or used as a memory region for an operation executed in the user terminal 100. The CPU 111, the ROM 112, and the RAM 113 are mutually connected to each other through an internal bus. Further, the controller 110 controls the communication module 120, the input/output module 130, the sensor unit 140, the storage unit 150, the power supplier 160, the screen 171, and the screen controller 172. In addition, the controller 110 may be implemented by a single core or a plurality of cores such as a dual core, a triple core, or a quadruple core processor. The number of cores may be configured differently according to characteristics of the terminal.

The controller 110 receives a selection of a media content to be uploaded to a content sharing server (not shown) from the user and uploads the media content to the content sharing server. Further, the controller 110 receives information regarding a user input from the content sharing server and stores the information regarding the user input to be linked with the media content. When the media content is displayed, the information regarding the user input stored and linked with the media content may be also displayed.

The communication module 120 may include (not shown) at least one of a cellular module, a wireless Local Area Network (LAN) module, and a short distance communication module.

A cellular module enables the user terminal 100 to be connected with an external device through mobile communication by using one or more antennas according to a control of the controller 110. The cellular module transmits/receives a wireless signal for a voice call, a video call, a Short Message Service (SMS), or a Multimedia Message Service (MMS) to/from a mobile phone (not shown), a smart phone (not shown), a tablet Personal Computer (PC), or another device (not shown) having a phone number input into the user terminal 100.

The wireless LAN module may access the Internet in a place where a wireless Access Point (AP) (not shown) is installed, according to a control of the controller 110. The wireless LAN module supports a wireless LAN standard (IEEE802.11x) of the Institute of Electrical and Electronics Engineers (IEEE). The wireless LAN module may drive a Wi-Fi Positioning System (WPS) that identifies position information on the terminal including the wireless LAN module by using position information provided by the wireless AP wirelessly connected with the wireless LAN module.

The short distance communication module wirelessly processes short distance communication with the user terminal 100 according to a control of the controller 110, and may process communication based on Bluetooth, Infrared Data Association (IrDA) communication, WiFi-Direct communication, or a short-distance communication scheme, such as Near Field Communication (NFC).

The input/output module 130 includes a button 131, a speaker 132, a vibration motor 133, and a keypad 134.

The button 131 may be formed on a front surface, a side surface or a rear surface of the housing of the user terminal 100 and may include at least one of (not shown) a power/lock button, a volume button, a menu button, a home button, a back button, and a search button.

The speaker 132 outputs sounds corresponding to various signals (e.g., a wireless signal, a broadcasting signal, etc.) of the cellular module, the wireless LAN module, and the short distance communication module to the outside of the user terminal 100 according to a control of the controller 110.

The vibration motor 133 converts an electronic signal to mechanical vibration according to a control of the controller 110. One or more vibration motors 164 may be formed within the housing of the user terminal 100.

The speaker 132 and the vibration motor 133 operate according to a setting state of a volume operation mode of the user terminal 100. For example, possible volume operation modes of the user terminal 100 may include a sound mode, a vibration mode, a sound/vibration mode, and a mute mode, and volume operation mode may be set as one of these example modes. The controller 110 may output a signal instructing the speaker 132 or the vibration motor 133 to execute an operation thereof according to a function performed by the user terminal 100 based on the set mode of the volume operation mode.

The keypad 134 receives key input from the user so as to control the user terminal 100. The keypad 134 includes a physical keypad (not shown) formed on the user terminal 100 or a virtual keypad (not shown) displayed on the screen 171. The physical keypad (not shown) formed on the user terminal 100 may be omitted depending on a capability or structure of the user terminal 100.

The storage unit 150 stores input/output signals or data corresponding to operations of the communication module 120, the input/output module 130, the sensor unit 140, and the screen 171 according to a control of the controller 110. The storage unit 150 may also store control programs and applications for controlling the user terminal 100.

Herein, the term "storage unit" may generally refer to elements including the storage unit 150, the ROM 112 and the RAM 113 within the controller 110, or a memory card (for example, a Secure Digital (SD) card or a memory stick) installed in the user terminal 100. The storage unit may include a non-volatile memory, a volatile memory, a Hard Disc Drive (HDD) or a Solid State Drive (SSD).

The power supplier 160 may supply power to one or more batteries (not shown) arranged at the housing of the user terminal 100 according to a control of the controller 110. The batteries supply power to the user terminal 100. Further, the power supplier 160 may supply power input from an external power source (not shown) through a wired cable (not shown) connected to a connector (not shown) included in the device to the user terminal 100. In addition, the power supplier 160 may supply, to the user terminal 100, power wirelessly input from an external power source through a wireless charging technology.

The screen 171 displays a user interface corresponding to various services (e.g., a call, data transmission, etc.) to the user based on an Operation System (OS) of the terminal. The screen 171 may transmit an analog signal corresponding to at least one touch input into the user interface to the screen controller 172. The screen 171 may receive at least one touch from a user's body (e.g., fingers including a thumb) or another touch input means (e.g., a stylus pen).

The screen 171 may be implemented as, for example, a resistive type, a capacitive type, an infrared type, or an acoustic wave type screen.

Meanwhile, the screen controller 172 controls output values of the screen 171 so that display data provided from the controller 110 is displayed on the screen 171. The screen controller 172 converts an analog signal received from the screen 171 to a digital signal (for example, X and Y coordinates) and transmits the converted digital signal to the controller 110. The controller 110 may control the screen 171 by using the digital signal received from the screen controller 172. For example, the controller 110 may allow a short-cut icon (not shown) displayed on the screen 171 to be selected or executed in response to a touch event or a hovering event. According to an alternative embodiment of the present invention, the screen controller 172 may be included in the controller 110.

Figure 6:
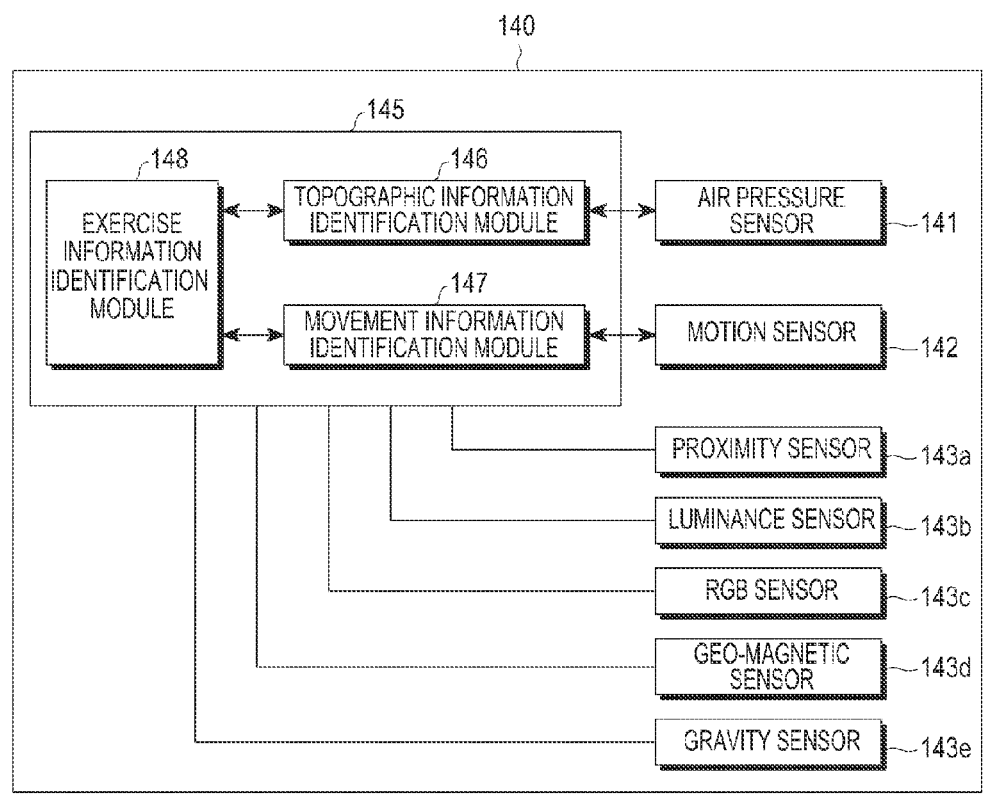
FIG. 6 is a block diagram illustrating a detailed configuration of a sensor unit of FIG. 5 according to an embodiment of the present invention.

FIG. 6 is a block diagram illustrating a detailed configuration of the sensor unit of FIG. 5. Referring to FIG. 6, the sensor unit 140 includes a motion sensor 141 that detects operations of the user terminal 100 (e.g., rotation of the user terminal 100 and acceleration or vibration applied to the user terminal 100) and an air pressure sensor 142 (e.g., an altimeter detecting an altitude) that measures atmospheric pressure.

The sensor unit 140 further includes at least one sensor that detects a surrounding environment of the user terminal 100. For example, the sensor unit 140 may selectively include a proximity sensor 143*a* that detects whether the user approaches the user terminal 100, a luminance sensor 143*b* that detects an amount of ambient light of the user terminal 100, an RGB sensor 143*c*, a geo-magnetic sensor 143*d* that detects a point of the compass by using the magnetic field on Earth, and a gravity sensor 143*e* that detects a gravity acting direction.

The sensor unit 140 may be implemented as a sensor hub in the form of a Micro Controller Unit (MCU) 145 including a separate processor that can process data provided from at least one sensor separated from the controller 110 but included within the sensor unit 140. The MCU 145 may include a processor (not shown) that processes data, a ROM storing a predetermined program controlling at least one sensor included in the sensor unit 140, and a RAM used for storing a signal or data generated while the predetermined program is executed or data provided from at least one sensor.

The MCU 145 includes a topographic information identification module 146, a movement information identification module 147, and an exercise information identification module 148 that perform the user exercise information identifying method according to the embodiment of the present invention.

The topographic information identification module 146 identifies topographic information by using air pressure information of the user terminal carried by the user. The air pressure information corresponds to information on pressure applied to the user terminal, and may be data (hereinafter referred to as "air pressure sensor data") measured and provided by the air pressure sensor 141 included in the user terminal. For example, since the air pressure sensor data is measured in units of a predetermined time, a wide variation of air pressure sensor data may be generated according to a movement state (e.g., walking, running, etc.) of the user. Accordingly, the topographic information identification module 146 applies the air pressure sensor data to a low pass filter having a predetermined size and collects low pass-filtered data for a predetermined time T, as shown in FIG. 2. Further, as shown in FIG. 2, the topographic information identification module 146 identifies a difference value D of air pressure sensor data between a start point and an end point of the predetermined time and information $\alpha$ on a change in the air pressure sensor data during the collection. The topographic information identification module 146 also identifies the topographic information by using the difference value D of the air pressure sensor data and the information $\alpha$ regarding the change in the air pressure sensor data.

The topographic information may include a topographic state indicating whether the topography where the user has moved is a flatland or a slope. The topographic state may be identified using the difference value D of the air pressure sensor data and the information $\alpha$ on the change in the air pressure sensor data, and more specifically, identified according to a degree of sloping determined using the difference value D of the air pressure sensor data and the information $\alpha$ regarding the change in the air pressure sensor data. When the degree of sloping identified using the difference value D of the air pressure sensor data and the information $\alpha$ on the change in the air pressure sensor data is at least equal to a predetermined threshold, the topographic information identification module 146 determines the topographic state as a "slope". When the degree of sloping is less than the predetermined threshold, the topographic information identification module 146 determines the topographic state as a "flatland".

The user may carry the user terminal in various ways, such as putting the user terminal into a bag, putting the user terminal into a pocket, or grasping the user terminal by hand while moving. As described above, as the user carries the user terminal in various ways while moving, the air pressure sensor data may be generated as different values. Further, according to an individual physical feature of the user or exercise intensity, the air pressure sensor data of the user terminal carried by the user may have different values. As variance of the air pressure sensor data is variously changed due to such various factors, a topographic state may be erroneously determined. According to an embodiment of the present invention, in order to reduce the error in the determination the topographic state, the topographic state may be determined after a reference corresponding to a predefined condition is variably changed.

Meanwhile, the movement information identification module 147 may identify the movement information by analyzing a vertical or horizontal movement of the user terminal carried and moved by the user. Further, the vertical or horizontal movement of the user terminal may be identified through sensor data input from the motion sensor 142 included in the user terminal. For example, the movement information may include a movement state, and the movement state may include information on a "running" state, a "walking" state, and the like. More specifically, the movement information identification module 147 may identify the movement information as the "running" state when a vertical or horizontal motion data (acceleration data) value provided from the motion sensor 142 (e.g., an acceleration sensor) included in the user terminal is at least equal to or a predetermined threshold, and identifies the movement information as the "walking" state when the motion data (acceleration data) value is less than the predetermined threshold.

Although according to certain embodiments of the present invention described herein, the movement information identification module 147 identifies the movement state as the "walking" state or the "running" state, embodiments of the present invention are not limited thereto. For example, the movement information identification module 147 may set the movement state as a "normal walking" state, a "quick walking" state, or a "running" state, and accordingly, the movement identification module 147 may set the predetermined threshold as a plurality of values for distinguishing between these states.

Further, although according to certain embodiments of the present invention described herein, the movement information identification module 147 determines the movement information by using the vertical or horizontal acceleration data value provided from the acceleration sensor, embodiments of the present invention are not limited thereto. More specifically, the user may carry the user terminal in various ways, such as putting the user terminal into a bag, putting the user terminal into a pocket, or grasping the user terminal by hand while moving. As described above, by taking into consideration, the various ways that the user may move while carrying the user terminal, the movement information identification module 147 is able to more accurately identify the movement information by using data provided from the gyro sensor or the geo-magnetic sensor. For example, by identifying and applying a direction in which the user moves, through the use of the data provided from the gyro sensor or the geo-magnetic sensor, the movement information identification module 147 is able to more accurately identify the movement information of the user terminal, even though the user carries the user terminal in various ways.

Further, the movement information may further include a step count. The movement information identification module 147 may identify the step count through a periodical pattern of the data provided from the acceleration sensor, the gyro sensor, or the geo-magnetic sensor.

For example, in response to a movement of the user, the data provided from the acceleration sensor, the gyro sensor, or the geo-magnetic sensor may have a predetermined periodic pattern. The predetermined periodic pattern may be a sinusoidal pattern repetitively oscillating between a maximum value, an origin, and a minimum value. Based on the pattern, the movement information identification module 147 may count one cycle of a sine waveform in the data provided by the acceleration sensor, the gyro sensor, or the geo-magnetic sensor as one step.

Further, the movement information identification module 147 may determine the movement state of the user in consideration of the step count. For example, according to the step count measured within a predetermined period of time, the movement state of the user may be determined as the "running" state or the "walking" state. That is, when the step count is detected as being less than or equal to 2.5 steps per second, the movement information identification module 147 may determine the movement state as the "walking" state, or when the step count is detected as being greater than 2.5 steps per second, the movement information identification module 147 may determine the movement state as the "running" state.

Meanwhile, the exercise information identification module 148 may identify exercise information (e.g., amount of exercise, calorie consumption, etc.) of the user by using the movement information of the user terminal 100 and the topographic information.

When the user does not actually move on their own, but instead moves due to being in a moving object (e.g., an elevator, an escalator, an automobile, a ship, etc.), the topographic state may be identified as a "slope" or a "flatland" by a change in a value input from the air pressure sensor. Accordingly, exercise information may be erroneously calculated even though the user does not actually move. Therefore, according to an embodiment of the present invention, the exercise information identification module 148 identifies the exercise information in consideration of the topographic information identified through the air pressure sensor and the movement state of the user identified through the motion sensor. For example, when the movement state of the user is the "running" state or the "walking" state, the amount of exercise and burnt calories of the user may be identified by determining whether the topographic state is a "slope" or a "flatland".

Further, the amount of exercise and burnt calories of the user may vary according to whether the user moves on a slope or flatland. When the user moves on a slope, the amount of exercise and burnt calories of the user may vary according to whether the user moves on an ascent of the slope or a descent of the slope. Further, when the user moves on the slope, the amount of exercise and burnt calories of the user may be different according to an angle of the slope. Accordingly, step 30 of identifying the exercise information may be performed in consideration of the topographic information identified in step 10 and the movement information identified in step 20. For example, the exercise information identification module 148 may identify the exercise information according to situations shown in Table 1 in consideration of the topographic information and the movement information. More specifically, as described above, a weight or a constant parameter value used for calculating the amount of exercise and burnt calories of the user may vary according to each of the situations shown in Table 1.

Meanwhile, the exercise information identification module 148 may detect the sloping angle by using a change in the air pressure identified while the user terminal is moving. More specifically, the exercise information identification module 148 identifies a length (hereinafter referred to as a "vertical movement distance") between a maximum point and a minimum point in an area where the user terminal has moved by using the pressure generated while the user terminal is moving. Further, the exercise information identification module 148 identifies a step count (StepCount) identified according to the movement of the user and multiplies the step count (StepCount) by a predetermined pace (StepLength) so as to identify a length (hereinafter, referred to as a "slope movement distance") of the slope where the user has moved. Thereafter, the exercise information identification module 148 may identify the sloping angle (SlopeAngle) by applying the vertical movement distance (MovingDistanceVertical) and the slope movement distance (MovingDistanceSlope) to a trigonometric function in consideration of a relation between the vertical movement distance and the slope movement distance. For example, the sloping angle (SlopeAngle) may be calculated using Equation (1) above. Further, the exercise information identification module 148 may identify the vertical movement distance (MovingDistanceVertical) according to Equation (2) above and the slope movement distance (MovingDistanceSlope) according to Equation (3).

The pace (StepLength) may vary according to the movement state of the user (i.e., the "running" state, the "walking" state, etc). Accordingly, in order to more accurately identify the slope movement distance, the movement state (i.e., the "running" state, the "walking" state, etc.) is reflected in the pace multiplied by the step count when the slope movement distance is detected. Therefore, the exercise information identification module 148 may further include an operation of calculating the pace (StepLength) when calculating the sloping angle and the calculation of the pace (StepLength) may be performed according to Equation (4) above.

Finally, as the exercise information, the exercise information identification module 148 may detect the sloping angle (SlopeAngle) and the slope movement distance (MovingDistanceSlope) as calculated above.

Further, the exercise information identification module 148 may further calculate calories (hereinafter referred to as "calorie consumption") burnt by the user by using the sloping angle (SlopeAngle) and the slope movement distance (MovingDistanceSlope), and the exercise information may further include the calculated calorie consumption. The calorie consumption calculated by the exercise information identification module 148 reflects the sloping angle (SlopeAngle) and may be used for more accurately predicting the amount of exercise of the user.

The MCU 145 controls an operation of detecting the exercise information according to a request of the controller 110. More specifically, in response to an execution of an application making a request for detecting the exercise information, the controller 110 sends a request for initiating or ending the detection of the exercise information to the MCU 145. Further, the MCU 145 controls the initiation or end of the operations of the topographic information identification module 146, the movement information identification module 147, and the exercise information identification module 148 in response to the request for initiating or ending the detection of the exercise information. Specifically, as the controller 110 makes the request for initiating the detection of the exercise information to the MCU 145, the MCU 145 initiates the operations of the topographic information identification module 146, the movement information identification module 147, and the exercise information identification module 148 to perform the operation of detecting the exercise information. As the controller 110 makes a request for providing the exercise information to the MCU 145, the MCU 145 provides the exercise information detected through the topographic information identification module 146, the movement information identification module 147, and the exercise information identification module 148 to the controller 110. Further, the detected exercise information may be accumulated and stored from an initiation time point until a time point when the exercise information is provided. This time period for detecting, accumulating, and storing the exercise information may correspond to a section (e.g., time, a place, etc.) according to request by the controller 110.

In another example according to an embodiment of the present invention, in response to the request for initiating the detection of the exercise information by the controller 110, the MCU 145 sets a predetermined section (e.g., three minutes) for which the exercise information is detected. The MCU 145 may store the exercise information for the predetermined section (e.g., three minutes) and provide the stored exercise information to the controller 110 at an interval of the predetermined section (e.g., three minutes).

In another example according to an embodiment of the present invention, the MCU 145 controls the operations of the topographic information identification module 146, the movement information identification module 147, and the exercise information identification module 148 in consideration of the "ON" or "OFF" state of the screen 171 of the user terminal 100 and provide the exercise information detected through the modules 146, 147, and 148 to the controller 110. For example, in response to the execution of the application requesting detection of the exercise information, the controller 110 requests detection of the exercise information to the MCU 145 and initiates the operations of the topographic information identification module 146, the movement information identification module 147, and the exercise information identification module 148 so as to perform the detection of the exercise information. When the screen 171 of the user terminal 100 is in the "ON" state, the MCU 145 provides the exercise information detected through the topographic information identification module 146, the movement information identification module 147, and the exercise information identification module 148 to the controller 110 whenever the step count is counted by the movement information identification module 147. However, when the screen 171 of the user terminal 100 is in the "OFF" state, the MCU 145 stores the exercise information detected through the topographic information identification module 146, the movement information identification module 147, and the exercise information identification module 148 for a predetermined time (e.g., twenty minutes) and provide the stored exercise information to the controller 110 periodically at an interval of the predetermined time (e.g., twenty minutes).

The "ON" or "OFF" state of the screen 171 included in the user terminal 100 may be identified by the controller 110. The controller 110 may provide an indication of the "ON" or "OFF" state of the screen 171 to the MCU 145 and the MCU 145 may control an operation of providing the exercise information to the controller 110 in consideration of the "ON" or "OFF" state of the screen 171. More specifically, when the controller 110 provides an indication of the "ON" state of the screen 171 to the MCU 145, the MCU 145 provides the detected exercise information to the controller 110, whenever the step count is counted by the movement information identification module 147. When the controller 110 provides the "OFF" state of the screen 171 to the MCU, the MCU 145 stores the exercise information for the predetermined time (e.g., twenty minutes) and provides the stored exercise information to the controller 110 periodically at an interval of the predetermined time (e.g., twenty minutes).

Although according to various embodiments of the present invention described herein, the MCU 145 provides the exercise information to the controller 110, embodiments of the present invention are not limited thereto, and the topographic information identified by the topographic information identification module 146 and the movement information identified by the movement information identification module 147 may be provided together with the exercise information.

Although according to various embodiments of the present invention described herein, the topographic information identification module 146 determines the topographic state as the "slope" state or the "flatland" state, embodiments of the present invention are not limited thereto. The topographic state may be variously changed by a designer. For example, the topographic state may be determined by stages based on a predetermined threshold of the sloping angle. For example, the topographic information identification module 147 may determine the topographic state as a predetermined stage topographic state, such as 1-1 stage topography when the sloping angle is greater than 0 degrees and less than or equal to 10 degrees, 1-2 stage topography when the sloping angle is greater than 0 degrees and less than or equal to −10 degrees, 2-1 stage topography when the sloping angle is greater than 10 degrees and less than or equal to 20 degrees, 2-2 stage topography when the sloping angle is greater than −10 degrees and less than or equal to −20 degrees, 3-1 stage topography when the sloping angle is greater than 20 degrees and less than or equal to 30 degrees, 3-2 stage topography when the sloping angle is greater than −20 degrees and less than or equal to −30 degrees, 4-1 stage topography when the sloping angle is greater than 30 degrees and less than or equal to 40 degrees, 4-2 stage topography when the sloping angle is greater than −30 degrees and less than or equal to −40 degrees, 5-1 stage topography when the sloping angle is greater than 40 degrees and less than or equal to 50 degrees, and 5-2 stage topography when the sloping angle is greater than −40 degrees and less than or equal to −50 degrees.

Although according to various embodiments of the present invention described herein, the movement information identification module 147 determines the movement state of the user as the "running" state or the "walking" state, embodiments of the present invention are not limited thereto. The movement state of the user may be variously changed by the designer. For example, the movement state of the user may be determined by stages based on a predetermined threshold. For example, the movement information identification module 147 may determine the movement state as a predetermined stage movement state, such as a first stage movement when the number of steps per unit time (e.g., one second) is greater than 0 and less than or equal to 1, a second stage movement when the number of steps per unit time (e.g., one second) is greater than 1 and less than or equal to 2, a third stage movement when the number of steps per unit time (e.g., one second) is greater than 2 and less than or equal to 3, a fourth stage movement when the number of steps per unit time (e.g., one second) is greater than 3 and less than or equal to 4, and a fifth stage movement when the step per unit time (e.g., one second) is greater than 4 and less than or equal to 5.

Embodiments of the present invention can be implemented in software, hardware, or a combination thereof. Any such software may be stored, for example, in a volatile or non-volatile storage device such as a ROM, a memory such as a RAM, a memory chip, a memory device, or a memory Integrated Circuit (IC), or a recordable optical or magnetic medium such as a Compact Disc (CD), a Digital Versatile Disc (DVD), a magnetic disk, or a magnetic tape, regardless of its ability to be erased or its ability to be re-recorded. It can be also appreciated that methods according to embodiments of the present invention may be implemented by a computer or a user terminal including a controller and a memory. The memory is one example of machine-readable devices suitable for storing a program or programs including instructions implementing the embodiments of the present invention. Accordingly, embodiments of the present invention include a program for a code implementing the apparatus and method described in the appended claims of the specification and a machine (a computer or the like)-readable storage medium for storing the program. Moreover, such a program as described above can be electronically transferred through an arbitrary medium such as a communication signal transferred through cable or wireless connection, and any equivalents.

Moreover, a mobile terminal according to embodiments of the present invention can receive and store a program from a program provision device that is connected thereto in a wired or wireless manner. A program providing apparatus may include a program including instructions to perform a preset contents protection method, a memory for storing information required for the contents protection method, a communication unit for performing wired or wireless communication, and a controller for controlling program transmission. When a program providing apparatus receives a request for providing the program from the user terminal, the program providing apparatus may provide the program to the user terminal through a wired or wireless connection. Further, even when there is no request for providing the program from the user terminal, for example, when the user terminal is located within a particular place, the program providing apparatus may provide the program to the user terminal.

While the invention has been shown and described with reference to certain embodiments thereof, it will be understood by those skilled in the art that various changes in form and detail may be made therein without departing from the spirit and scope of the invention as defined by the appended claims and their equivalents.

What is claimed is:

1. A method of identifying exercise information of a user of a user terminal, the method comprising:
   detecting air pressure information at a location of the user terminal;
   identifying information of a topography at the location of the user terminal by using the detected air pressure information;
   analyzing vertical movement and horizontal movement of the user terminal to identify movement information of the user terminal; and
   identifying the exercise information of the user according to the identified movement information of the user terminal and the identified information of the topography at the location of the user terminal,
   wherein the information of the topography includes a topographic state indicating a flatland or a slope.

2. The method of claim 1, wherein the movement information of the user includes a movement speed of the user.

3. The method of claim 2, wherein the movement information of the user includes a movement state of the user selected from a plurality of movement states including a walking state and a running state.

4. The method of claim 3, wherein the movement information of the user includes a movement distance determined according to the movement state, a step count, and a pace of the user.

5. The method of claim 3, wherein identifying the movement information comprises identifying the movement state of the user based on a step count detected within a predetermined time period.

6. The method of claim 1, wherein the movement information reflects data measured, by a motion sensor including an acceleration sensor and an air pressure sensor, at each instance of predetermined time interval, to analyze the vertical and horizontal movement of the user terminal.

7. The method of claim 6, wherein the motion sensor further includes at least one of a gyro sensor and a geo-magnetic sensor.

8. The method of claim 1, wherein the movement information of the user includes a step count.

9. The method of claim 1, wherein the state of the topography includes a topography sloping angle.

10. The method of claim 9, wherein the exercise information of the user includes calorie consumption of the user calculated in consideration the topography sloping angle.

11. A user terminal identifying exercise information of a user, the user terminal comprising:
an air pressure sensor configured to detect air pressure information at a location of the user terminal;
a motion sensor configured to detect vertical movement and horizontal movement of the user terminal; and
a sensor processor configured to process a program for identifying exercise information of the user by using data detected from the air pressure sensor and the motion sensor,
wherein the program for identifying the exercise information of the user comprises a command for identifying information of a topography at the location of the user terminal by using the detected air pressure information, analyzing the vertical movement and the horizontal movement of the user terminal to identify movement information of the user terminal, and identifying the exercise information of the user according to the identified movement information of the user terminal and the identified information of the topography at the location of the user terminal,
wherein the information of the topography includes a topographic state indicating a flatland or a slope.

12. The user terminal of claim 11, further comprising a screen configured to display information,
wherein the program for identifying the exercise information of the user provides the exercise information to the controller in accordance to an operation state of the screen.

13. The user terminal of claim 12, wherein the movement information of the user includes a movement state of the user selected from a plurality of movement states including a walking state and a running state.

14. The user terminal of claim 13, wherein the movement information of the user includes a movement distance determined according to the movement state, a step count, and a pace of the user.

15. The user terminal of claim 13, wherein the movement information is identified based on a step count detected within a predetermined unit period.

16. The user terminal of claim 11, wherein the program for identifying the exercise information of the user identifies the exercise informaiton according to the data detected from the air pressure sensor and the motion sensor at each instance of a predetermined time interval, to analyze the vertical and horizontal movement of the user terminal.

17. The user terminal of claim 16, wherein the motion sensor further includes at least one of a gyro sensor and a geo-magnetic sensor.

18. The user terminal of claim 11, wherein the movement information of the user includes a step count.

19. The user terminal of claim 11, wherein the information of the topography includes a topography sloping angle.

20. The user terminal of claim 19, wherein the exercise information of the user includes calorie consumption of the user calculated in consideration of the topography sloping angle.

* * * * *